(12) United States Patent
Suzuki

(10) Patent No.: US 8,693,620 B2
(45) Date of Patent: Apr. 8, 2014

(54) X-RAY COMPUTED TOMOGRAPHY APPARATUS

(75) Inventor: Tatsuro Suzuki, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/097,634

(22) Filed: Apr. 29, 2011

(65) Prior Publication Data

US 2011/0286574 A1 Nov. 24, 2011

(30) Foreign Application Priority Data

May 21, 2010 (JP) .................................. 2010-117736

(51) Int. Cl.
*A61B 6/03* (2006.01)

(52) U.S. Cl.
USPC ............................................................ 378/8

(58) Field of Classification Search
USPC ............................................. 378/8; 382/131
See application file for complete search history.

(56) References Cited

U.S. PATENT DOCUMENTS

| | | | | |
|---|---|---|---|---|
| 4,903,704 A * | 2/1990 | Van Eggermond et al. | ... | 600/413 |
| 6,298,111 B1 * | 10/2001 | Ozaki | ................................. | 378/8 |
| 6,470,208 B1 * | 10/2002 | Woodford et al. | ............ | 600/428 |
| 6,708,052 B1 * | 3/2004 | Mao et al. | ..................... | 600/407 |
| 7,313,213 B1 * | 12/2007 | Hsieh et al. | ........................ | 378/8 |
| 7,885,374 B2 * | 2/2011 | Noshi et al. | ........................ | 378/8 |
| 2005/0089133 A1 * | 4/2005 | Tsuyuki | ............................. | 378/8 |
| 2006/0274878 A1 * | 12/2006 | Hsieh et al. | ........................ | 378/8 |
| 2007/0237289 A1 * | 10/2007 | Deller et al. | ........................ | 378/8 |
| 2008/0063137 A1 * | 3/2008 | Hsieh et al. | ........................ | 378/8 |
| 2008/0165919 A1 * | 7/2008 | Bruder et al. | ........................ | 378/8 |

FOREIGN PATENT DOCUMENTS

| | | |
|---|---|---|
| CN | 1927123 A | 3/2007 |
| JP | 2002-191595 | 7/2002 |
| JP | 2003-245272 | 9/2003 |
| JP | 2010-046212 | 3/2010 |

OTHER PUBLICATIONS

Office Action issued Jul. 3, 2012, in Chinese Patent Application No. 201110131376.2 with English translation.
Office Action mailed Jan. 7, 2014 in Japanese Application No. 2010-117736, filed May 21, 2010 (with English-Language Translation), 4 pages.

* cited by examiner

*Primary Examiner* — Irakli Kiknadze
(74) *Attorney, Agent, or Firm* — Oblon, Spivak, McClelland, Maier & Neustadt, L.L.P.

(57) ABSTRACT

According to one embodiment, an X-ray computed tomography apparatus includes an X-ray tube, X-ray detector, acquisition unit, rotating mechanism, input unit, and control unit. The input unit repeatedly inputs trigger signals originating from a specific phase of a periodic motion of a body of a subject or a periodic motion of an organ of the subject. The trigger signals being supplied from a measuring device which measures the periodic motion. The control unit causes the X-ray tube to start generating X-rays on the basis of the input of a first trigger signal of the repeatedly input trigger signals, and causes the X-ray tube to stop generating X-rays on the basis of the input of a second trigger signal next to the first trigger signal in order to repeatedly scan the subject over substantially one period of the movement while a scan position is fixed.

26 Claims, 13 Drawing Sheets

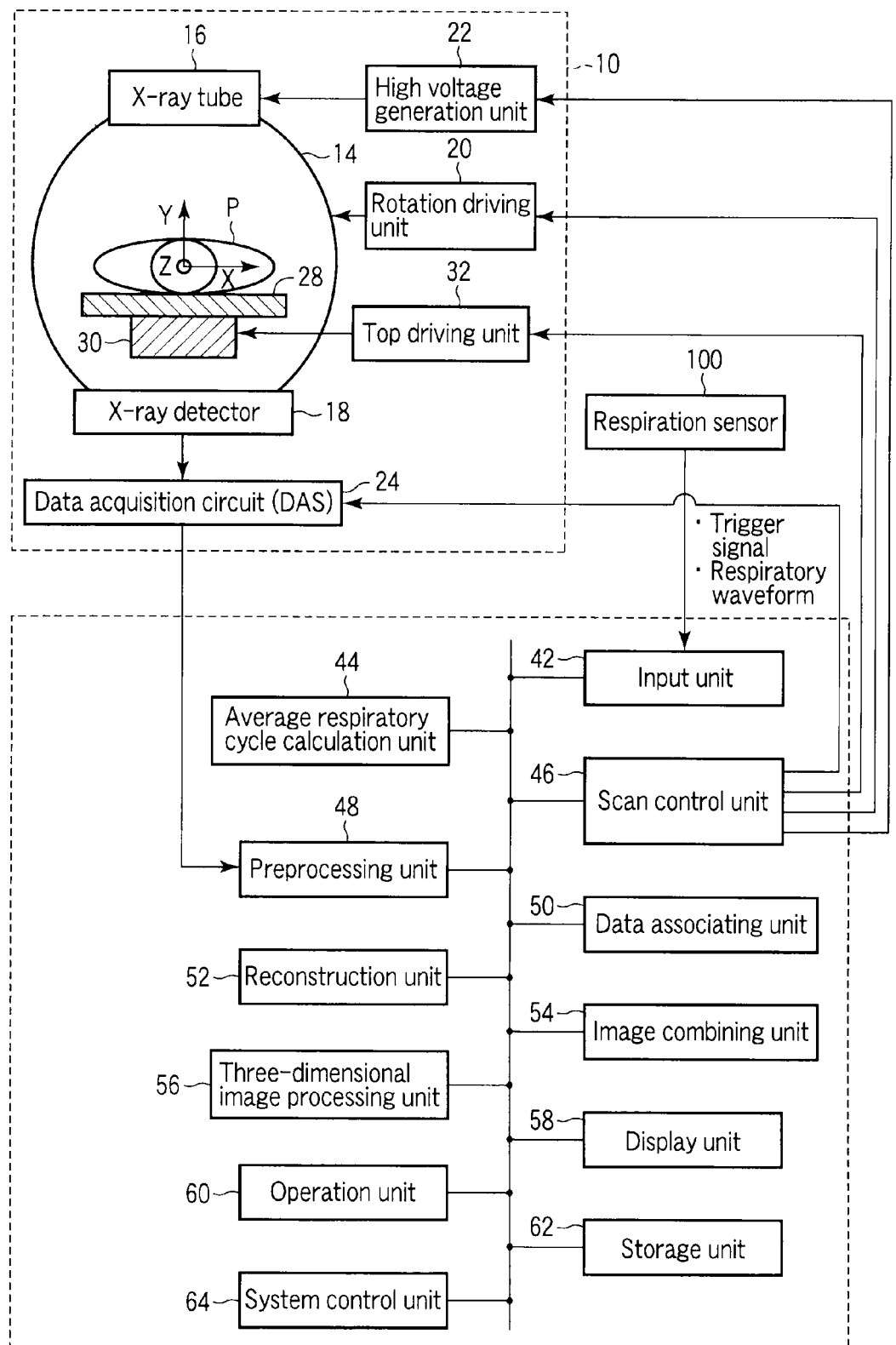
F I G. 1

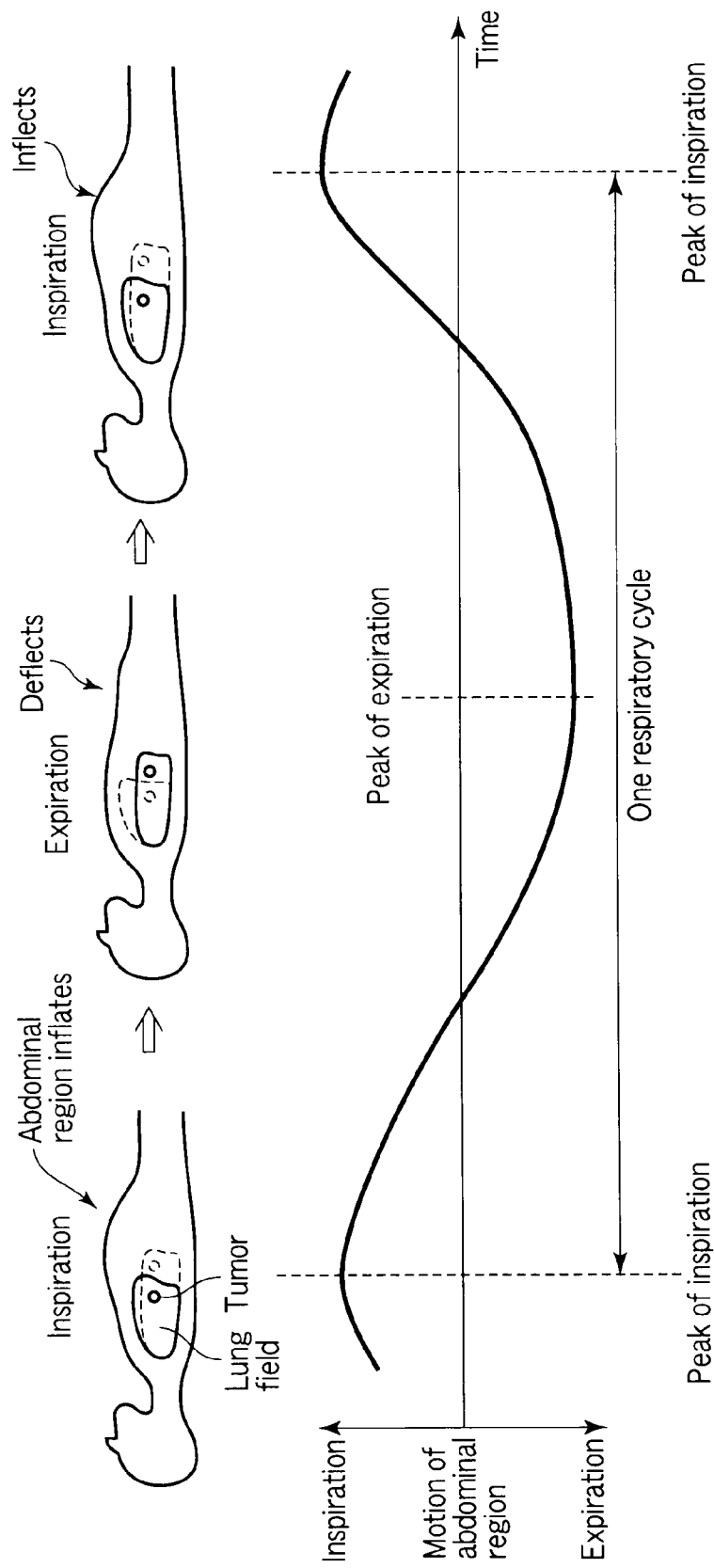
F I G. 3

Respiration sensor constituted by combination of laser length measuring device and computer

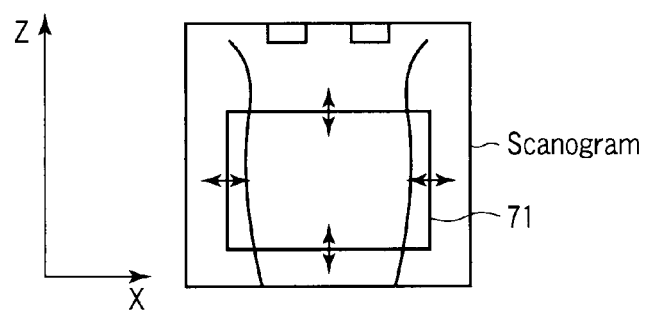
F I G. 10
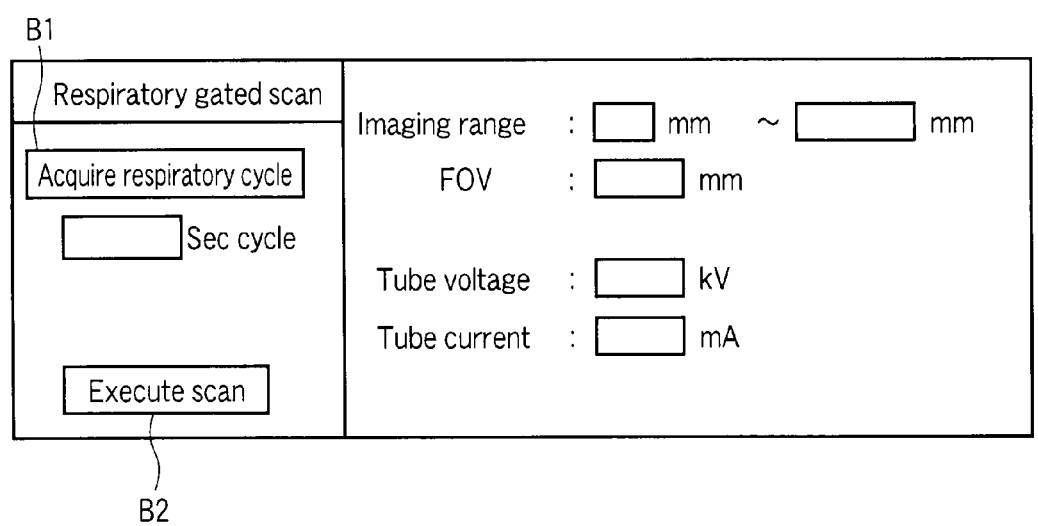
F I G. 11

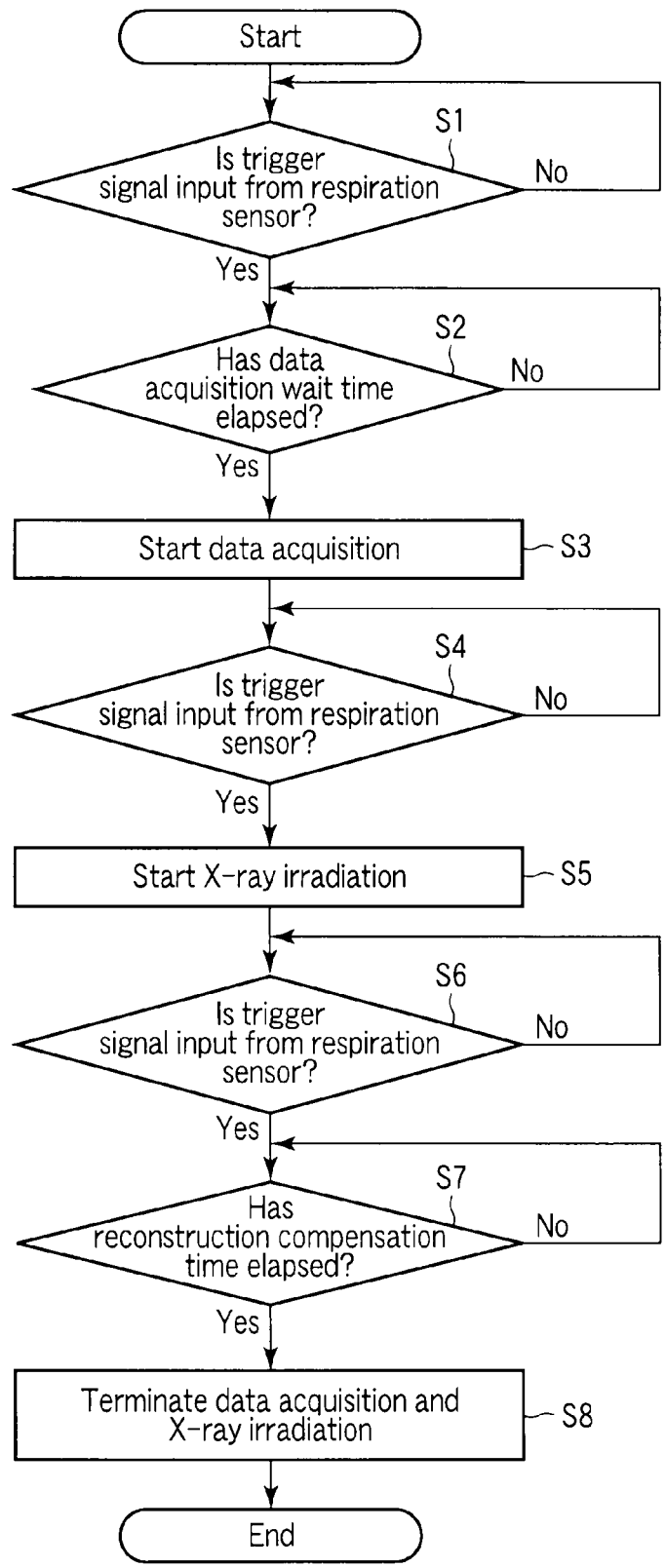
F I G. 12

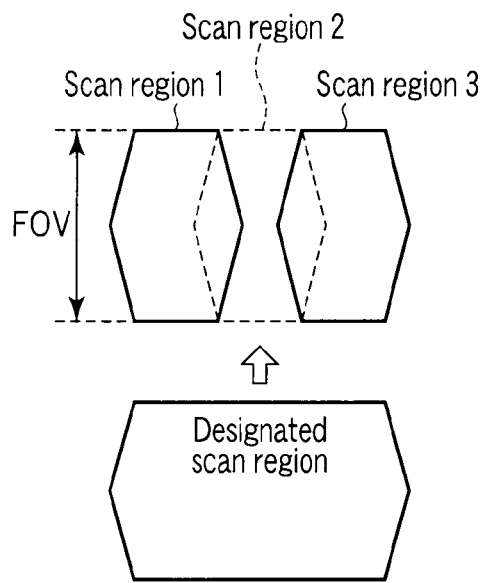
F I G. 16
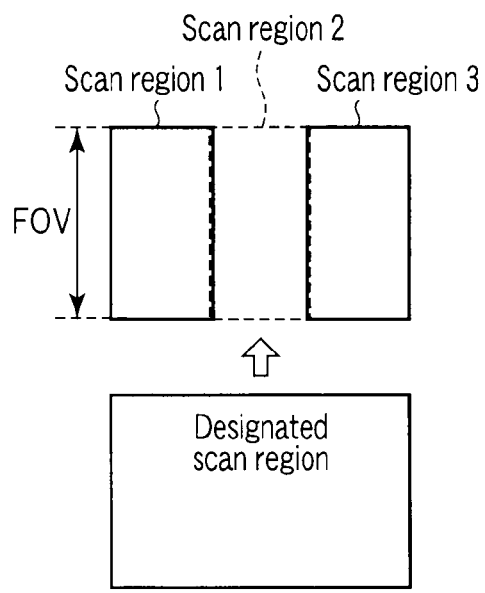
F I G. 17

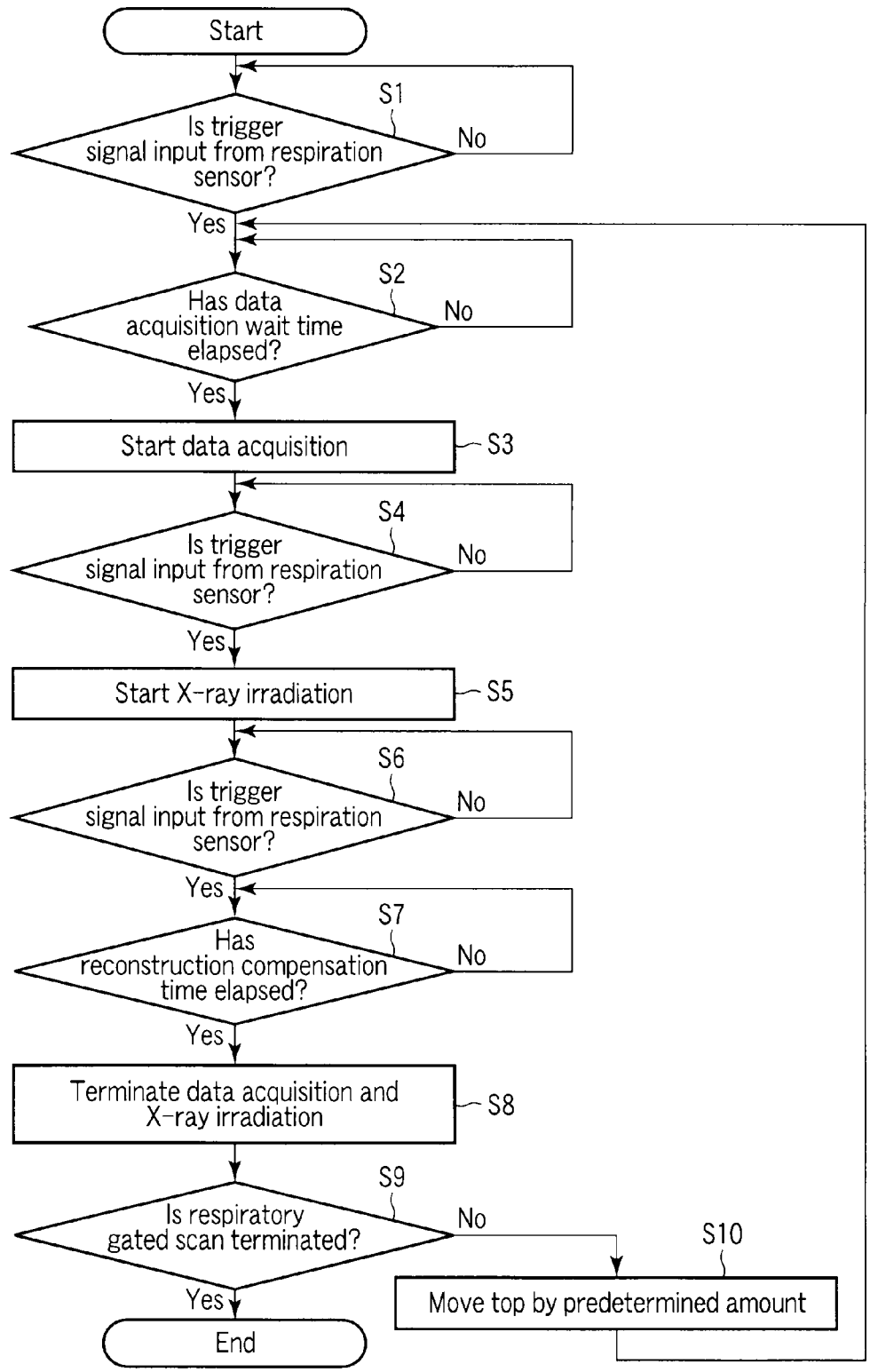
F I G. 18

X-RAY COMPUTED TOMOGRAPHY APPARATUS

CROSS-REFERENCE TO RELATED APPLICATIONS

This application is based upon and claims the benefit of priority from Japanese Patent Application No. 2010-117736, filed May 21, 2010; the entire contents of which are incorporated herein by reference.

FIELD

Embodiments described herein relate generally to an X-ray computed tomography apparatus.

BACKGROUND

Dynamic scan is one of the scan schemes used by X-ray computed tomography apparatuses. Dynamic scan is a scheme of repeatedly scanning a scan region at the same position while the top position is fixed. Dynamic scan allows to observe temporal changes in the same scan region. For example, dynamic scan is often used to observe movements and blood flow dynamics in a subject.

When acquiring image data corresponding to at least one respiratory cycle by a dynamic scan, the operator needs to determine by himself/herself an X-ray irradiation start timing and an X-ray irradiation stop timing. Subjects differ in respiratory motion. Even the same subject undergoes changes in respiratory motion in different situations at different times. An attempt to accurately execute a dynamic scan corresponding to only one respiratory cycle may quicken the irradiation stop timing to result in insufficient scan time. In addition, an attempt to avoid a lack of scan time may quicken the irradiation start timing. As a consequence, the scan time may exceed one respiratory cycle. As described above, it is difficult to accurately execute a dynamic scan corresponding to one respiratory cycle.

BRIEF DESCRIPTION OF THE DRAWINGS

FIG. 1 is a view showing the arrangement of an X-ray computed tomography apparatus according to an embodiment;

FIG. 3 is a view showing the relationship between the respiratory motion of a subject and the motion of the abdominal region which are measured by a measuring device in FIG. 1;

FIG. 10 is a view showing an example of a scanning condition setting window displayed by a display unit in FIG. 1;

FIG. 11 is a view showing an example of a scanning condition setting window displayed by the display unit in FIG. 1;

FIG. 12 is a flowchart showing a typical procedure for control processing for a respiratory gated dynamic scan by a system control unit according to the first embodiment;

FIG. 16 is a view showing an example of the shape of a scan region associated with a respiratory gated dynamic scan according to the second embodiment;

FIG. 17 is a view showing an example of a scan region associated with a respiratory gated dynamic scan according to the second embodiment;

FIG. 18 is a flowchart showing a typical procedure for control processing for a respiratory gated dynamic scan performed by a system control unit according to the second embodiment.

DETAILED DESCRIPTION

In general, according to one embodiment, an X-ray computed tomography apparatus includes an X-ray tube, X-ray detector, acquisition unit, rotating mechanism, input unit, control unit, and reconstruction unit. The X-ray tube generates X-rays. The X-ray detector detects X-rays generated from the X-ray tube and transmitted through a subject and generates an electrical signal corresponding to the detected X-rays.

The acquisition unit acquires the projection data corresponding to the electrical signal via the X-ray detector. The rotating mechanism rotatably supports the X-ray tube and the X-ray detector around the subject. The input unit repeatedly inputs trigger signals originating from a specific phase of a periodic motion of a body of the subject or a periodic motion of an organ of the subject. The trigger signals being supplied from a measuring device which measures the periodic motion. The control unit causes the X-ray tube to start generating X-rays on the basis of an input of a first trigger signal of the repeatedly input trigger signals, and causes the X-ray tube to stop generating X-rays on the basis of an input of a second trigger signal next to the first trigger signal in order to repeatedly scan the subject over substantially one period of the movement while a scan position is fixed. The reconstruction unit reconstructs data of an image associated with the subject based on the projection data.

An X-ray computed tomography apparatus (to be referred to as an X-rays CT apparatus hereinafter) according to this embodiment will be described blow with reference to the views of the accompanying drawing.

Note that X-ray CT apparatuses include a rotate/rotate-type apparatus in which an X-ray tube and an X-ray detector rotate together around a subject, and a stationary/rotate-type apparatus in which many detectors are arranged in the form of a ring, and only an X-ray tube rotates around a subject. The embodiment can be applied to either type. In this case, the rotate/rotate type will be exemplified.

Figure 2:
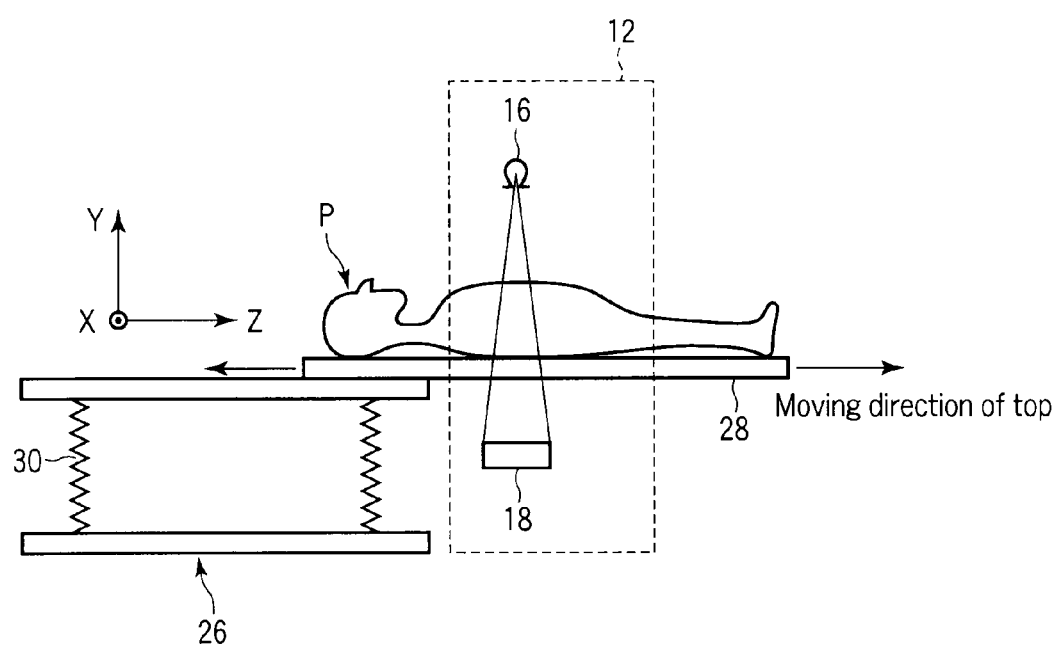
FIG. 2 is a view showing an outer appearance of a scanning mechanism in FIG. 1.

FIG. 1 is a view showing the arrangement of an X-ray CT apparatus according to this embodiment. As shown in FIG. 1, the X-ray CT apparatus includes a scanning mechanism 10 and an image processing apparatus 40. FIG. 2 is a view showing an outer appearance of the scanning mechanism 10.

As shown in FIGS. 1 and 2, the scanning mechanism 10 includes a gantry 12 for scanning a subject P with X-rays. An annular or disk-like rotating frame 14 is mounted on the gantry 12. The rotating frame 14 supports an X-ray tube 16 and an X-ray detector 18 so as to make them rotatable around the body axis of a subject P. Note that the subject P is placed to make the body axis of the subject almost coincide with the rotation axis of the rotating frame. In other words, the rotating frame 14 supports the X-ray tube 16 and the X-ray detector 18 so as to make them rotatable around the rotation axis. The rotating frame 14 is connected to a rotation driving unit 20. The rotation driving unit 20 rotates the rotating frame 14 under the control of a scan control unit 46 in the image processing apparatus 40, and rotates the X-ray tube 16 and the X-ray detector 18 around the body axis of the subject P.

Note that the Z-axis is defined by the rotation axis of the rotating frame 14. The Y-axis is defined by an axis connecting the X-ray focus of the X-ray tube 16 to the center of the detecting surface of the X-ray detector 18. The Y-axis is perpendicular to the Z-axis. The X-axis is defined by an axis perpendicular to the Y- and Z-axes. In this manner, the XYZ orthogonal coordinate system forms a rotational coordinate system which rotates together with the rotation of the X-ray tube 16.

The X-ray tube 16 generates an X-ray cone beam upon receiving a high voltage from a high voltage generation unit 22. The high voltage generation unit 22 applies a high voltage to the X-ray tube 16 under the control of the scan control unit 46.

The X-ray detector 18 detects the X-rays generated from the X-ray tube 16 and transmitted through the subject P, and generates an electrical signal corresponding to the intensity of the detected X-rays.

As the X-ray detector 18, a detector of a type called an area detector or multi-row detector may be used. The X-ray detector 18 of this type includes a plurality of X-ray detection elements arrayed two-dimensionally. For example, 1,000 X-ray detection elements are arrayed along an arc centered on the Z-axis. The array direction of these X-ray detection elements is called a channel direction. A plurality of X-ray detection elements arrayed along the channel direction is called an X-ray detection element row. For example, 64 X-ray detection element rows are arrayed along the slice direction indicated by the Z-axis. A data acquisition circuit (DAS: Data Acquisition System) 24 is connected to the X-ray detector 18.

The data acquisition unit 24 reads out an electrical signal for each channel from the X-ray detector 18 under the control of the scan control unit 46. The data acquisition circuit 24 generates projection data as a digital signal by amplifying the read electrical signal and digitally converting the amplified electrical signal. Note that the data acquisition circuit 24 can also generate projection data by reading out an electrical signal from the X-ray detector 18 in a period during which no X-rays are irradiated. The generated projection data is supplied to the image processing apparatus 40 via a noncontact data transmission unit (not shown).

A bed 26 is placed near the gantry 12. The bed 26 includes a top 28, a top support mechanism 30, and a top driving unit 32. The subject P is placed on the top 28. The top support mechanism 30 supports the top 28 so as to make it movable along the Z-axis. Typically, the top support mechanism 30 supports the top 28 so as to make its long axis parallel to the Z-axis. The top driving unit 32 drives the top support mechanism 30 to move the top 28 along the Z-axis direction under the control of a scan control unit 47.

A measuring device 100 is connected to the image processing apparatus 40 via a cable or the like. The measuring device 100 is a respiration sensor which measures the respiratory motion of the subject P. The measuring device 100 typically measures the motion of the body surface accompanying respiratory motion, more specifically, the motion of the abdominal region, to measure the respiratory motion.

FIG. 3 is a view showing the motion of the abdominal region accompanying respiratory motion. As shown in FIG. 3, in general, inspiration inflates the abdominal region, and expiration deflates the abdominal region. Accompanying respiratory motion, the positions and shapes of internal organs change. For example, the position and shape of the lung fields greatly change accompanying respiration. That is, the tumor developed in the lung fields also greatly changes accompanying respiration. The time from a given inspiration to the next inspiration is called a respiratory cycle. The respiratory cycle changes depending on how the subject breathes. That is, the respiratory cycle is not constant, and each respiratory cycle differs in duration. Note that the definition of a respiratory cycle in this embodiment is not limited to this. For example, the time from a given expiration to the next expiration may be defined as one respiratory cycle.

As the measuring device 100, it is possible to use, for example, a combination of a laser length measuring device which measures the motion of the abdominal region of the subject P and a computer.

Figure 4:
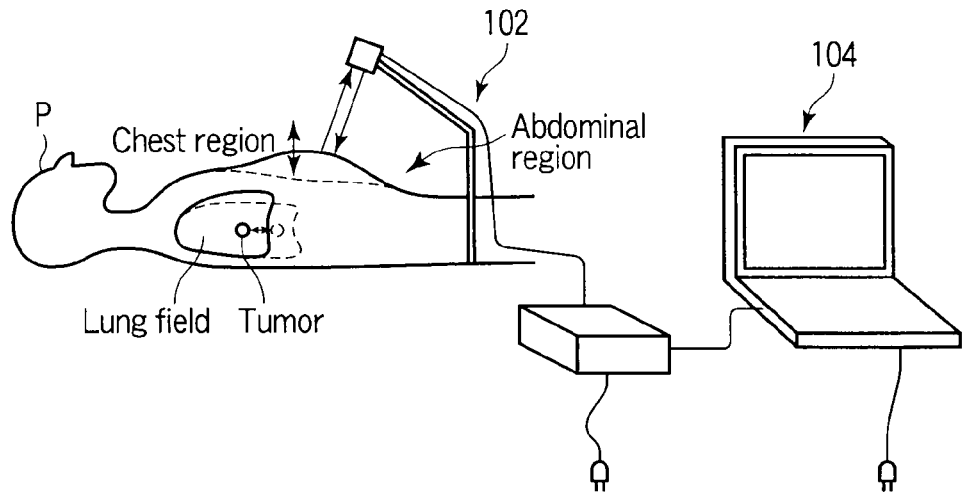
FIG. 4 is a view showing an outer appearance of the measuring device in FIG. 1 which is constituted by a combination of a laser length measuring device and a computer.

FIG. 4 is a view showing an outer appearance of the measuring device 100 constituted by a combination of a laser length measuring device 102 and a computer 104. As shown in FIG. 3, the laser length measuring device 102 measures the motion of the abdominal region with laser light. The laser length measuring device 102 supplies the measurement value to the computer 104. The computer 104 measures respiratory motion in real time based on the supplied measurement value. Typically, the computer 104 monitors measurement values in real time and generates a respiratory waveform indicating temporal changes in measurement value. The computer 104 also monitors measurement values in real time and generates a trigger signal in response to the arrival of the respiratory motion of the subject at one specific respiratory phase on a respiratory waveform. A trigger signal is set to be generated at one specific phase of a plurality of respiratory phases. The data of the respiratory waveform and the trigger signal are supplied to the image processing apparatus 40 of the X-ray CT apparatus.

Figure 5:
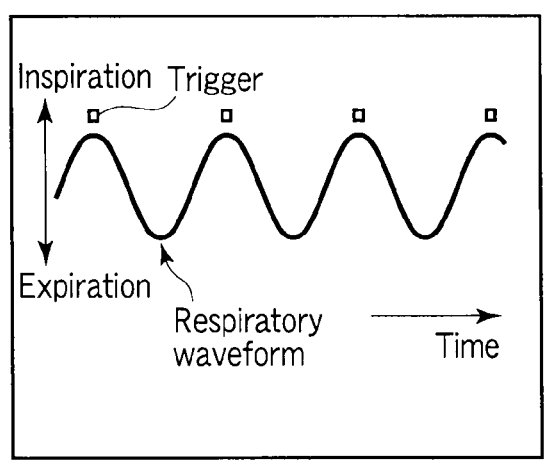
FIG. 5 is a graph showing the relationship between the respiratory waveform generated by the measuring device in FIG. 1 and trigger signals.

FIG. 5 is a graph showing the relationship between the respiratory waveform and trigger signals generated by the measuring device 100. As shown in FIG. 5, a respiratory waveform is a graph with the abscissa being defined by the time, and the ordinate the measurement values. The measurement value is set to increase as, for example, the position of the abdominal region surface rises, and vice versa. A trigger signal is generated in response to, for example, the arrival of a measurement value at or near a vertex point (peak) of a respiratory waveform. In this case, the trigger signal corresponds to a respiratory phase at the time point when the subject breathes most deeply. The computer 104 displays this respiratory waveform and a mark indicating a trigger on the measuring device 100 while superposing them on each other.

Note that the measuring device 100 according to this embodiment is not limited to the type using a laser length measuring device. For example, the measuring device 100 may be of a type using a pressure sensor. In this case, the pressure sensor is attached between the abdominal region of the subject and a band wound around the abdominal region. The pressure sensor repeatedly measures the pressure acting between the band and the abdominal region. The measurement values are supplied to the computer connected to the pressure sensor. This computer monitors measurement values from the pressure sensor and measures pressure changes, thereby measuring respiratory motion.

The measuring device 100 according to this embodiment may be of a type using an optical camera. In this case, the optical camera repeatedly images a light reflecting member placed on the abdominal region. The optical camera supplies image data to the computer connected to the optical camera. This computer monitors the position of the light reflecting member based on the image data from the optical camera, and measures the motion of the light reflecting member, thereby measuring respiratory motion.

Note that the measuring device 100 according to this embodiment is not limited to the above types. The measuring device according to this embodiment may be of any type that can measure the respiratory motion of the subject (the states of expiration and inspiration).

The image processing apparatus 40 includes an input unit 42, an average respiratory cycle calculation unit 44, the scan control unit 46, a preprocessing unit 48, a data associating unit 50, a reconstruction unit 52, an image combining unit 54, a three-dimensional image processing unit 56, a display unit 58, an operation unit 60, a storage unit 62, and a system control unit 64.

The input unit 42 inputs respiratory waveform data and trigger signals from the measuring device 100. The system control unit 64 senses the input data of the respiratory waveform and trigger signals. Note that it is not always necessary to input respiratory waveform data.

The average respiratory cycle calculation unit 44 calculates the average respiratory cycle of the subject P based on trigger signals and a respiratory waveform. An average respiratory cycle is used to set a data acquisition wait time (to be described later).

The scan control unit 46 implements a scan method unique to this embodiment, i.e., dynamic scan synchronized with respiration (to be referred to as respiratory gated dynamic scan hereinafter) to execute a dynamic scan over nearly one respiratory cycle. More specifically, the scan control unit 46 controls the generation of X-rays from the X-ray tube 16 and the acquisition of projection data by the data acquisition circuit 24 in synchronism with a trigger signal from the measuring device 100 in order to perform a dynamic scan on the subject P over nearly one respiratory cycle (i.e., to repeatedly scan the same scan region over nearly one respiratory cycle while the scan position is fixed). More specifically, the scan control unit 46 causes the X-ray tube 16 to start generating X-rays on the basis of the input of a trigger signal to the input unit 42, and causes the X-ray tube 16 to stop generating X-rays on the basis of the input of the next trigger signal to the input unit 42.

The scan control unit 46 also controls the generation of X-rays from the X-ray tube 16, the acquisition of projection data by the data acquisition circuit 24, and the intermittent movement of the top 28 by the top support mechanism 30 in synchronism with a trigger signal from the measuring device 100 in order to perform a dynamic scan on each of a plurality of scan regions associated with the subject over nearly one respiratory cycle (i.e., to repeatedly perform a scan at each scan position over nearly one respiratory cycle while intermittently moving the top 28 to each scan position; in other words, to repeatedly perform a dynamic scan and move the top). More specifically, the scan control unit 46 causes the X-ray tube 16 to start generating X-rays on the basis of the input of a trigger signal to the input unit 42, causes the X-ray tube 16 to stop generating X-rays on the basis of the input of the next trigger signal to the input unit 42, and also causes the top 28 to move by a predetermined amount.

A preprocessing unit 48 performs preprocessing such as logarithmic transformation and sensitivity correction for the projection data supplied from the data acquisition circuit 24.

The data associating unit 50 associates projection data with a trigger signal based on the acquisition time of the projection data (the rotational angle of the X-ray tube 16: view) and the time of the generation of the trigger signal. The storage unit 62 stores the projection data with which the trigger signal is associated.

The reconstruction unit 52 reconstructs the data of a plurality of CT images associated with a plurality of respiratory phases based on projection data. As the data of a CT image according to this embodiment, three-dimensional image data (volume data) associated with one volume or tomogram data (slice data) associated with one slice can be used. Assume that, for the sake of a concrete description, the data of a CT image is the data of a three-dimensional image. In this case, the reconstruction unit 52 may perform image reconstruction in consideration of a cone angle. This will generate the data of a three-dimensional image with higher accuracy. The reconstruction unit 52 can also reconstruct the data of a three-dimensional image associated with the respiratory phase designated by the operator via the operation unit 60. In addition, when the apparatus performs a dynamic scan on each of a plurality of scan regions, the reconstruction unit can reconstruct the data of a plurality of three-dimensional images associated with the scan regions.

Image reconstruction methods include a full reconstruction method and a half reconstruction method. The full reconstruction method requires projection data corresponding to one rotation around a subject, i.e., about $2\pi$ [rad], to reconstruct the data of a three-dimensional image of one volume. The half scan method requires projection data corresponding to $\pi+\alpha$ [rad] ($\alpha$: fan angle) to reconstruct the data of a three-dimensional image of one volume. The operator can arbitrarily set an image reconstruction method to be used via the operation unit 60.

The image combining unit 54 generates the data of a single composite three-dimensional image associated with the scan regions based on the data of three-dimensional images associated with the scan regions.

The three-dimensional image processing unit 56 generates the data of a two-dimensional display image by performing three-dimensional image processing for the data of a three-dimensional image or the data of a composite three-dimensional image.

The display unit 58 displays the display image on the display device. The display unit 58 also displays, on the display device, a setting window for setting a scan plan for a respiratory gated dynamic scan according to this embodiment. As the display device, for example, a CRT display, liquid crystal display, organic EL display, plasma display, or the like can be used as needed.

The operation unit 60 accepts various kinds of commands and information inputs from the operator via an input device. As the input device, a keyboard, a mouse, switches, or the like can be used.

The storage unit 62 stores the projection data with which trigger signals are associated, the data of CT images, and the data of display images. The storage unit 62 may also store an average respiratory cycle. In addition, the storage unit 62 stores a control program for the X-ray CT apparatus. This control program is used to make the system control unit 64 execute the control function of the X-ray CT apparatus for the execution of a respiratory gated dynamic scan according to this embodiment.

The system control unit 64 functions as the main unit of the X-ray CT apparatus. More specifically, the system control unit 64 reads out the control program stored in the storage unit 62 and expands it to control each unit in accordance with the expanded control program.

Figure 6:
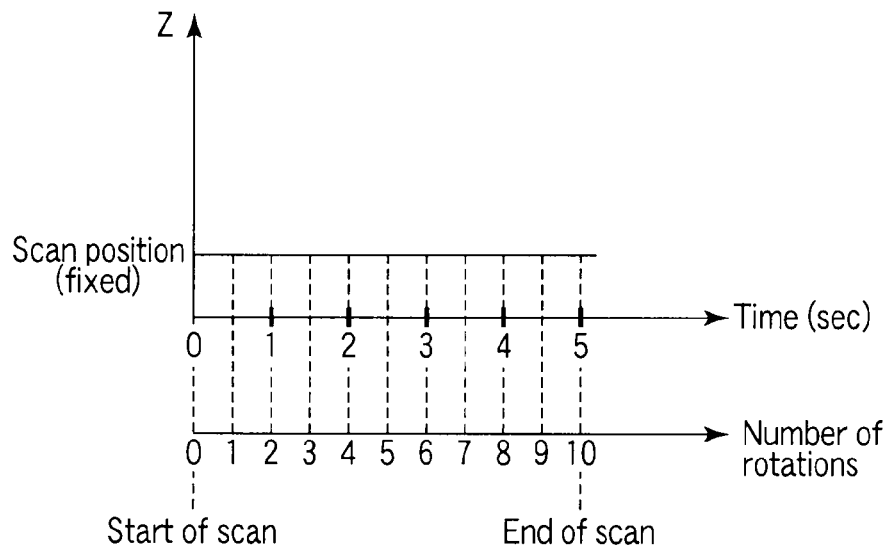
FIG. 6 is a graph showing the relationship between the scan position and the time which are associated with dynamic scan according to this embodiment.

The respiratory gated dynamic scan implemented under the control of the system control unit 64 will be described in detail below. Dynamic scan as the basis of the respiratory gated dynamic scan according to this embodiment will be described first with reference to FIG. 6. FIG. 6 is a graph showing the relationship between the scan position and the time in a dynamic scan. As shown in FIG. 6, the scan position, i.e., the top position, is fixed in a dynamic scan. As described above, in a dynamic scan, scanning is repeated at the same scan position, and hence it is possible to observe temporal changes in a scan region in the body of the subject P on a display image. Assume that the scan position is the Z position on the top 28 which is located vertically below the focus of the X-ray tube 16.

In this case, one respiratory cycle (in other words, the time interval between a given trigger and the next trigger) is normalized to 100% to express respiratory phases in percentage. Assume that this embodiment acquires the data of a three-dimensional image at 10% intervals from 0% to 99%. That is, a dynamic scan corresponding to one respiratory cycle acquires the data of 10 three-dimensional images associated with 10 respiratory phases. In this case, the rotating frame 14 (i.e., the X-ray tube 16 and the X-ray detector 18) makes 10 rotations. Assuming that if one rotation takes 0.5 sec, a scan is performed at one scan position for 5 sec. Note that the numerical value "10%" is presented for a concrete description, and this embodiment is not limited to this. Any numerical value such as 5% or 20% can be set. That is, it is possible to acquire any number of three-dimensional images during one respiratory cycle.

Figure 7:
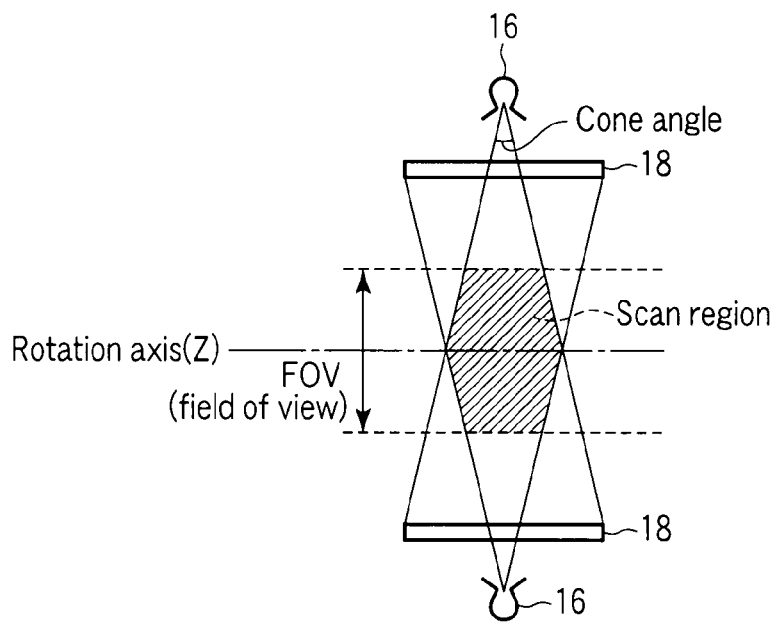
FIG. 7 is a view showing an example of the shape of a scan region according to this embodiment.
Figure 8:
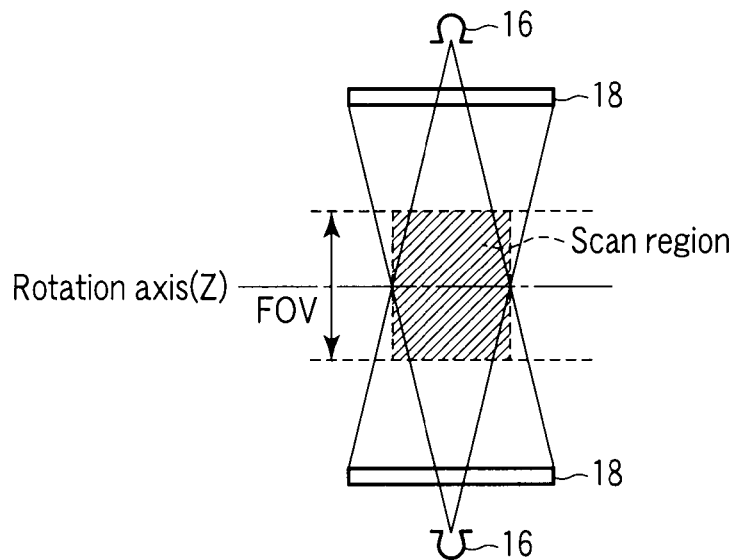
FIG. 8 is a view showing an example of the shape of a scan region according to this embodiment.
Figure 9:
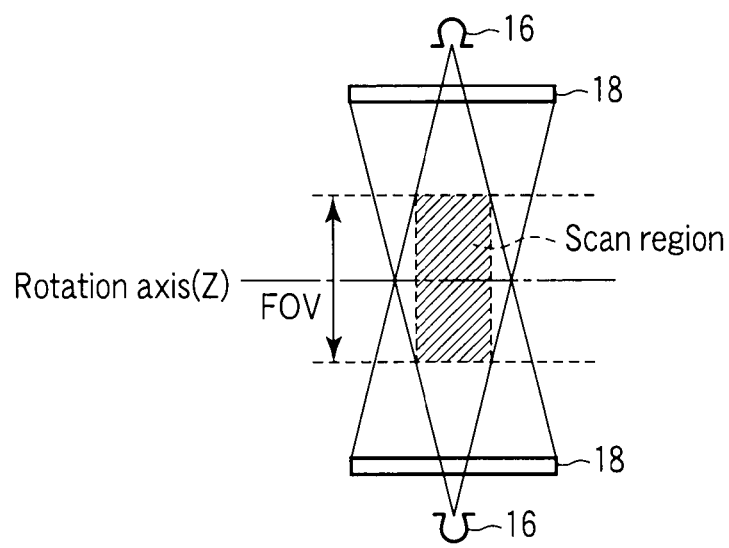
FIG. 9 is a view showing an example of the shape of a scan region according to this embodiment.

The shape of a scan region (reconstruction region) according to this embodiment will be described next. FIGS. 7, 8, and 9 are views each showing the pattern of the shape of a scan region. If the X-ray detector 18 is an area detector, the reconstruction unit 52 performs reconstruction in consideration of a cone angle. The scan regions shown in FIGS. 7 and 9 indicate regions which can be reconstructed by the full reconstruction method. The scan region shown in FIG. 8 indicates a region which can be reconstructed by the half reconstruction method. The scan region shown in FIG. 7 has a hexagonal shape on a Z-Y plane, and has a shape formed by rotating a trapezoid on the base through 360° in a three-dimensional space. The scan regions in FIGS. 8 and 9 each have a rectangular shape on an X-Y plane, and have a columnar shape in a three-dimensional space. Even when using the full reconstruction method, if the cone angle is small, it is possible to use a cylindrical region as a reconstruction region as shown in FIG. 8. Note that the range of a scan region (imaging range) need not always be identical to the range of a reconstruction region (reconstruction range). A reconstruction region can be set in an arbitrary range within a scan region.

The respiratory gated dynamic scan performed under the control of the system control unit 64 will be described in detail separately in the first embodiment and the second embodiment. The first embodiment will exemplify a scheme of performing a dynamic scan on one scan region while the position of the top 28 is fixed. The second embodiment will exemplify a scheme of performing a dynamic scan on each of a plurality of scan regions by intermittently moving the top 28 (a respiratory gated dynamic scan in a wide range).

First Embodiment

An example of the operation of an X-ray CT apparatus in a respiratory gated dynamic scan according to the first embodiment will be described below.

First of all, before the start of a respiratory gated dynamic scan, the operator sets scanning conditions via an operation unit 60. FIGS. 10 and 11 are views each showing an example of a scanning condition setting window. FIG. 10 shows a setting window for an imaging range of scanning conditions. A rectangle 71 indicating an imaging range is superimposed on a scanogram. The operator can move each side of the rectangle 71 with a mouse or the like. The operator can set an imaging range by dragging each side of the rectangle 71 with the mouse. The size of the set imaging range and the size of an FOV are respectively displayed in the imaging range display field and FOV display field in FIG. 11. Note that it is also possible to set an imaging range with numerals. In this case, an imaging range is reflected on a scanogram in accordance with input numerical values. It is possible to set other scanning conditions such as a tube voltage and a tube current via the operation unit 60.

An X-ray CT apparatus and a measuring device 100 according to this embodiment are connected to each other before the start of a respiratory gated dynamic scan. The measuring device 100 outputs a trigger signal and respiratory waveform data to an input unit 42 in real time. An average respiratory cycle calculation unit 44 calculates an average respiratory cycle based on a trigger signal and a respiratory waveform at the stage before a respiratory gated dynamic scan. More specifically, first of all, the operator presses an "acquire respiratory cycle" button B1 displayed on the setting window in FIG. 11. The average respiratory cycle calculation unit 44 receives trigger signals corresponding to a predetermined number of respirations and respiratory waveform data from the input unit 42 in response to the pressing of the button B1. It is possible to set the predetermined number of respirations to an arbitrary numeral such as "5". The average respiratory cycle calculation unit 44 then calculates the average respiratory cycle of the subject based on the trigger signals corresponding to the predetermined number of respirations and the respiratory waveform. The calculated average respiratory cycle is displayed in the "average respiratory cycle" field on the setting window in FIG. 11.

Upon completion of preparation for a respiratory gated dynamic scan, the operator presses an "execute scan" button B2 displayed on the setting window in FIG. 11. The system control unit 64 starts a respiratory gated dynamic scan in response to the pressing of the button B2.

Figure 13:
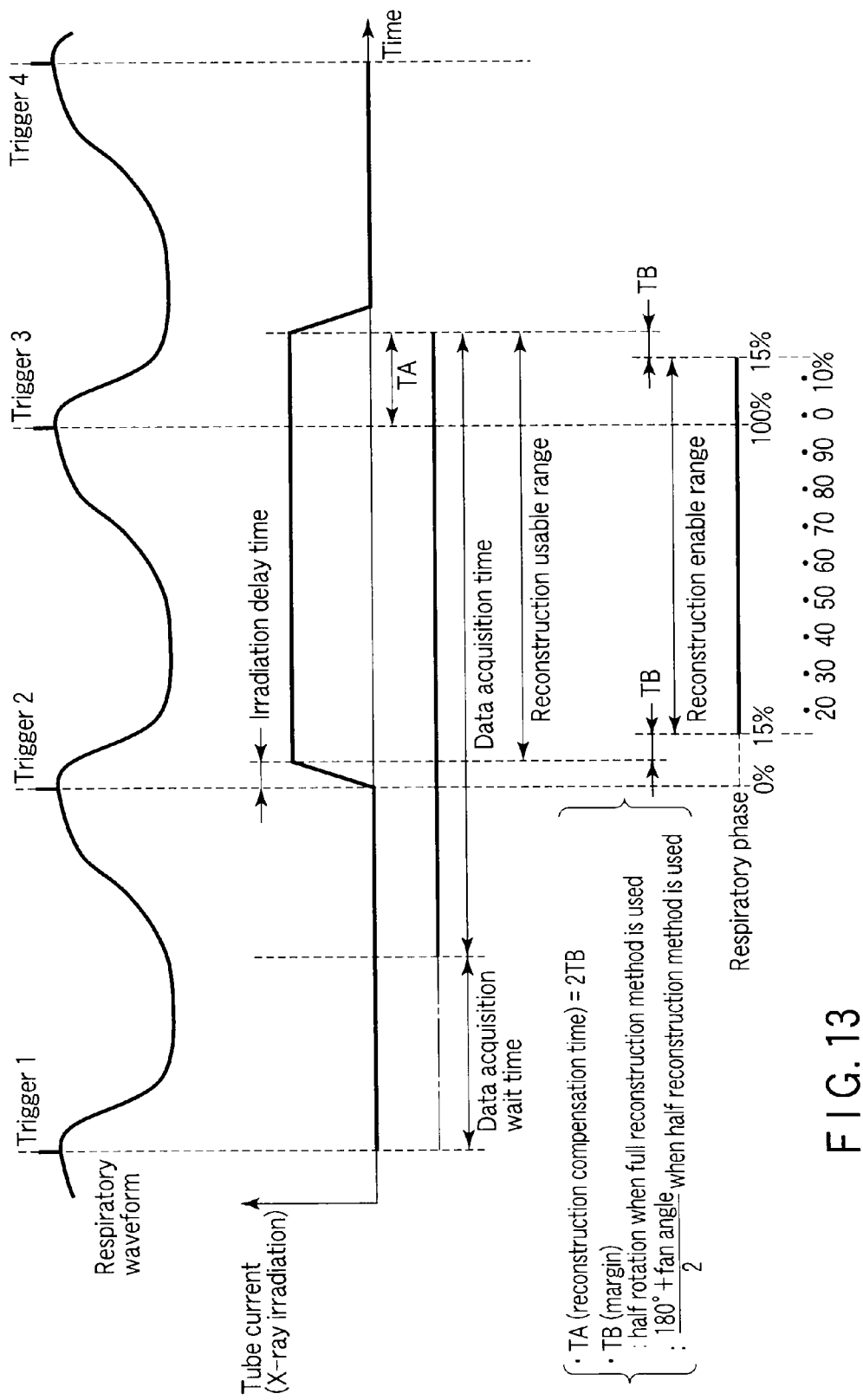
FIG. 13 is a sequence chart associated with the respiratory gated dynamic scan in FIG. 12.

FIG. 12 is a flowchart showing a typical procedure for control processing for a respiratory gated dynamic scan by the system control unit 64 according to the first embodiment. FIG. 13 is a sequence chart associated with a respiratory gated dynamic scan according to the first embodiment.

First of all, the system control unit 64 waits for the input of a trigger signal (first trigger signal) from the measuring device 100 (step S1). Upon inputting the first trigger signal, a system control unit 64 waits until the lapse of a predetermined data acquisition wait time from the input of the first trigger signal (step S2). A scan control unit 46 sets a data acquisition wait time based on an average respiratory cycle. For example, the scan control unit 46 sets the data acquisition wait time to a time corresponding to 60% of the average respiratory cycle. In this case, the data acquisition wait time is set to a time of the average respiratory cycle·(3/5). Note that the data acquisition wait time is not limited to only 60% of the average respiratory cycle. Even with variations in the respiratory cycle of the subject, the data acquisition wait time is set to the time from the instant the first trigger signal is input to the instant the next trigger signal (second trigger signal) is input.

In response to the lapse of the data acquisition wait time from the input of the first trigger signal (YES in step S2), the system control unit 64 causes the scan control unit 46 to start acquiring data (step S3). In step S3, the scan control unit 46 controls a data acquisition circuit 24 to start acquiring projection data. At this time point, the apparatus does not start X-ray irradiation. Acquiring projection data from the stage before X-ray irradiation can reliably associate the second trigger signal with the projection data afterward. This makes it possible to improve the accuracy of specifying projection data (projection data immediately after X-ray irradiation) at the reconstruction stage.

When the acquisition of projection data starts, the system control unit 64 waits for the input of the next trigger signal (second trigger signal) from the measuring device 100 (step S4). When the second trigger signal is input (YES in step S4), the system control unit 64 controls the scan control unit 46 to start X-ray irradiation (step S5). More specifically, the scan control unit 46 outputs, to a high voltage generation unit 22, an instruction to start generating X-rays on the basis of the input of the second trigger signal. Upon receiving the instruction to start, the high voltage generation unit 22 supplies a high voltage to an X-ray tube 16 to irradiate X-rays. The start time of X-ray irradiation is the time immediately before the input of the second trigger signal. In practice, the time from the instant the second trigger signal is input to the instant X-ray irradiation starts needs to include 1. the time from the instant the computer (system control unit 64) in the X-ray CT apparatus senses the second trigger signal to the instant the scan control unit 46 issues, to the high voltage generation unit 22, an instruction to start X-ray irradiation, and 2. the time from the instant a tube current is increased to the instant the tube current is stabilized at a set value. For this reason, the apparatus starts X-ray irradiation several 10 ms after the generation of the second trigger signal. The apparatus uses, for reconstruction, the projection data acquired by using X-rays generated by the stable tube current. Assume that the shortest time from the instant a trigger signal is detected to the instant a tube current is stabilized is called an irradiation delay time. That is, the apparatus generates X-rays for scanning after the lapse of the irradiation delay time from the input of a trigger signal. This embodiment automatically issues an instruction to start X-ray irradiation immediately after the input of a trigger signal. This facilitates control of the start timing of X-ray irradiation as compared with the prior art in which the detection timing of the next trigger signal is predicted from the detection timing of a given trigger signal, and an instruction to start X-ray irradiation is issued at the predicted timing.

Note that the scan control unit 46 may issue, to the high voltage generation unit 22, an instruction to generate X-rays at the same time when the second trigger signal is input to the input unit 42.

When X-ray irradiation starts, the system control unit 64 waits for the input of the next trigger signal (third trigger signal) from the measuring device 100 (step S6). When the third trigger signal is input (YES in step S6), the system control unit 64 waits until the lapse of a reconstruction compensation time TA from the input of the third trigger signal (step S7). The reconstruction compensation time TA is a data acquisition time provided due to the theoretical limitation of reconstruction. The reconstruction compensation time TA will be described in detail below.

When a reconstruction unit 52 is to acquire the data of a three-dimensional image associated with a respiratory phase by using the full reconstruction method, only projection data corresponding to one respiratory cycle centered on a respiratory phase as a reconstruction target is insufficient. This operation further theoretically requires projection data corresponding to a total of one rotation including projection data corresponding to the first half rotation of the X-ray tube 16 relative to the center and projection data corresponding to the second half rotation relative to the center. In this case, the time required for the X-ray tube 16 to make half rotation will be referred to as a time TB. That is, when acquiring the data of a three-dimensional image associated with a given respiratory phase, the apparatus requires "time corresponding to one respiratory cycle centered on respiratory phase as reconstruction target+2·TB" as the total time of X-ray irradiation. That is, the reconstruction compensation time TA is set to 2·TB. Note that the reconstruction compensation time TA may also be set to the total time of the time 2·TB required for the X-ray tube to make one rotation and an irradiation delay time. The irradiation delay time used for the reconstruction compensation time TA may be a value determined according to an empirical rule or a value determined in accordance with an actually measured irradiation delay time. Adding an irradiation delay time allows to execute a dynamic scan corresponding to nearly one respiratory cycle more accurately.

When the reconstruction unit 52 is to acquire the data of a three-dimensional image associated with a given respiratory phase by using the half reconstruction method, only projection data corresponding to one respiratory cycle centered on a respiratory phase as a reconstruction target is insufficient. This operation further theoretically requires projection data corresponding to a total of (180°+fan angle α) including projection data corresponding to first half angle [(180°+fan angle α)/2] relative to the center and projection data corresponding to second half angle [(180°+fan angle α)/2] relative to the center. Therefore, the total time for X-ray irradiation needs to be a time 2·TB (β:the time required for the X-ray tube 16 to make a half rotation and a rotation of the fan angle α) corresponding to time for one respiratory cycle+(180°+fan angle α). That is, the reconstruction compensation time TA is set to the time 2·TB required for the X-ray tube 16 to make a half rotation and a rotation of the fan angle α. Note that the reconstruction compensation time TA may be set to the total time of the time 2·TB required for the X-ray tube 16 to make a half rotation and a rotation of the fan angle α and the irradiation delay time. The irradiation delay time used for the reconstruction compensation time TA may be a value determined according to an empirical rule or a value determined in accordance with an actually measured irradiation delay time.

Note that the measuring device 100 does not always generate a trigger signal for each identical respiratory phase. For example, even if it is set to generate a trigger signal at the peak of each inspiration in the above operation, a trigger signal is not always generated at the peak of each inspiration, and the generation timings sometimes vary slightly. It is possible to set the reconstruction compensation time TA in consideration of such variations in trigger signal generation timing. In this case, the reconstruction compensation time TA is set to 2·β+irradiation delay time+trigger variation time. A trigger variation time may be set to a fixed value determined based on an empirical rule. Adding a predetermined trigger variation time allows to accurately execute a dynamic scan corresponding to nearly one respiratory cycle.

In response to the lapse of the reconstruction compensation time TA from the input of the third trigger signal (YES in step S7), the system control unit 64 controls the scan control unit 46 to stop the dynamic scan (step S8). In step S8, the scan control unit 46 controls the data acquisition circuit 24 to stop the acquisition of projection data, and controls the high voltage generation unit 22 to stop the X-ray irradiation.

Upon completion of step S8, the system control unit 64 terminates the control processing for the respiratory gated dynamic scan according to the first embodiment.

Upon termination of the control processing for the respiratory gated dynamic scan, the reconstruction unit 52 reconstructs the data of a plurality of three-dimensional images associated with a plurality of respiratory phases designated by the operator based on the acquired projection data. For example, with regard to the respiratory phases between trigger 2 and trigger 3, trigger 3 is set to 100% with reference to trigger 2 (0%). Likewise, with regard to the respiratory phases between trigger 3 and trigger 4, trigger 4 is set to 100% with reference to trigger 3 (0%). Respiratory phases are designated by the percentages predetermined in this manner.

Figures 14, 15:
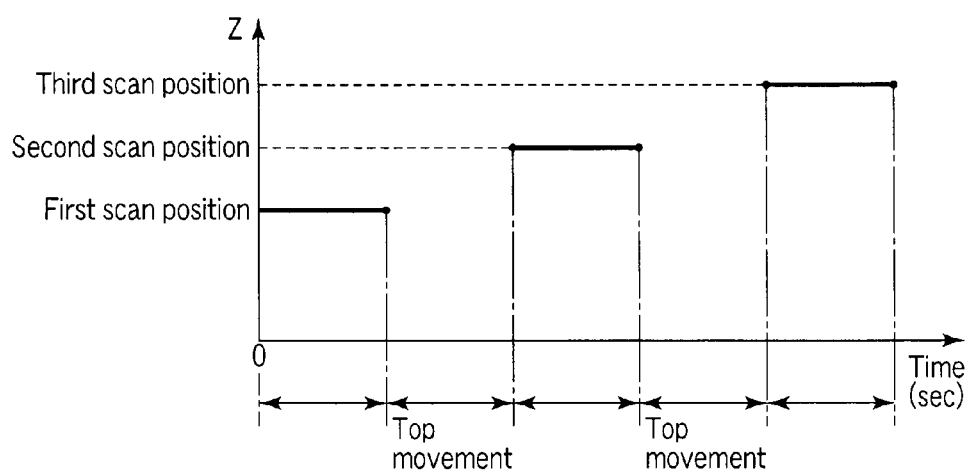
FIG. 14 is a view showing an example of a setting window for a reconstruction range and a respiratory phase as a reconstruction target which are displayed on the display unit in FIG. 1.
FIG. 15 is a graph showing the relationship between the scan position and the time which are associated with a dynamic scan accompanying top movement according to the second embodiment.

The operator can arbitrarily set a reconstruction range and a respiratory phase as a reconstruction target via the operation unit 60. FIG. 14 is a view showing an example of a setting window for a reconstruction range and a respiratory phase as a reconstruction target, which is displayed on a display unit 58. In general, a reconstruction range is automatically set in accordance with an imaging range. When the operator wants to set a reconstruction range in a range narrower than an imaging range, he/she can set it via the operation unit 60. With regard to respiratory phases, the operator can designate a respiratory phase at the start of reconstruction, a reconstruction interval, and a respiratory phase at the end of reconstruction in percentage. When, for example, reconstructing data for every 10% from 0% to 90%, the operator may input "0%" in the reconstruction start respiratory phase field, "90%" in the reconstruction interval field, and "10%" in the reconstruction end respiratory phase field. Note that the number of respiratory phases as reconstruction targets is not limited to plural. For example, it is possible to reconstruct data associated with one respiratory phase of one respiratory cycle.

As shown in FIG. 13, the acquisition time range (usable reconstruction time) for projection data which can be used for reconstruction corresponds to the time range from an X-ray irradiation start time point (more precisely, the time point when a tube current is stabilized) to an X-ray irradiation stop time point (more precisely, the time point when the tube current begins to decrease). A respiratory phase time range (possible reconstruction time) that can be used for reconstruction is limited more than a usable reconstruction time. That is, the possible reconstruction time is shorter than the usable reconstruction time by 2·TB. More specifically, the start time of the possible reconstruction time is at a time point TB after the start time of the usable reconstruction time. The end time of the possible reconstruction time is at a time point TB before the end time of the usable reconstruction time. A respiratory phase as a reconstruction target is set within this possible reconstruction time.

When performing full reconstruction, the reconstruction unit 52 extracts projection data corresponding to one rotation centered on a respiratory phase as a reconstruction target from acquired projection data, and reconstructs the data of a three-dimensional image based on the extracted projection data. When performing half reconstruction, the reconstruction unit 52 extracts projection data corresponding to 180°+fan angle α centered on a respiratory phase as a reconstruction target from acquired projection data, and reconstructs the data of a three-dimensional image based on the extracted projection data.

In this manner, the data of a plurality of three-dimensional images associated with a plurality of respiratory phases is reconstructed. When identical respiratory phases appear between trigger 2 and trigger 3 and between trigger 3 and trigger 4 (more specifically, the reconstruction compensation time TA), the identical respiratory phases are redundantly reconstructed. To prevent redundant reconstruction of three-dimensional images associated with this single respiratory phase, the apparatus allows to select one of a respiratory phase between trigger 2 and trigger 3 and a respiratory phase between trigger 3 and trigger 4 as a reconstruction target. For example, the operator may set, via the operation unit 60, one of respiratory phases as a reconstruction target which corresponds to either an earlier scan time or a later scan time. When a respiratory phase corresponding to the earlier scan time is to be set, a respiratory phase between trigger 2 and trigger 3 is used as a reconstruction target.

When the data of a three-dimensional image is reconstructed, a three-dimensional image processing unit 56 generates the data of a display image by performing three-dimensional image processing for the reconstructed data of the three-dimensional image. As three-dimensional image processing, for example, volume rendering, surface rendering, MPR, or pixel value projection method is used. The operator sets the type of three-dimensional image processing to be used in advance via the operation unit 60. Upon reconstruction of the data of a plurality of display images associated with a plurality of respiratory phases, the three-dimensional image processing unit 56 may perform three-dimensional image processing in accordance with the same image processing conditions. When, for example, performing volume rendering, the same viewpoint position/viewpoint direction may be used. When performing MPR, the same slice position may be used.

The display unit 58 displays a generated display image. Upon reconstruction of the data of a plurality of display images associated with a plurality of respiratory phases, the display unit 58 displays a plurality of display images along the chronological order of respiratory phases. More specifically, the display unit 58 displays the display images sequentially from 0%.

With the above arrangement, the X-ray CT apparatus according to the first embodiment controls X-ray irradiation start and stop timings based on the generation timing of a trigger signal of a respiratory waveform (the input timing for the X-ray CT apparatus). More specifically, the X-ray CT apparatus according to the first embodiment starts X-ray irradiation immediately after the input of a trigger signal. This makes it possible to easily control the X-ray irradiation start timing and start X-ray irradiation at a proper timing in accordance with the respiratory motion of the subject as compared with the prior art in which the detection timing of the next trigger signal is predicted from the detection timing of a given trigger signal, and an instruction to start X-ray irradiation is issued at the predicted timing. However, even if the apparatus is to start X-ray irradiation immediately after the input of a trigger signal, the apparatus may not start X-ray irradiation immediately after the input of a trigger signal in practice, that is, may not emit X-rays for a scan immediately after the input of a trigger signal. In order to compensate for this delay, the X-ray CT apparatus according to the first embodiment stops X-ray irradiation after the lapse of a compensation time from the input of the next trigger signal. That is, providing a compensation time (reconstruction compensation time, reconstruction compensation time+irradiation delay time, or reconstruction compensation time+irradiation delay time+trigger variation time) can compensate for the delay time of the start timing.

In this manner, the X-ray CT apparatus according to the first embodiment can generate X-rays immediately after the input of a trigger signal, and keep generating X-rays only within nearly one respiratory cycle starting immediately after the input of a trigger signal. The X-ray CT apparatus can therefore secure a scan time corresponding to nearly one respiratory cycle without excess or deficiency in accordance with changes in the respiratory motion of the subject. Therefore, the X-ray CT apparatus according to the first embodiment can execute a dynamic scan on the subject over nearly one respiratory cycle upon minimizing the exposure dose of the subject.

Second Embodiment

An example of the operation in a respiratory gated dynamic scan in a wide range according to the second embodiment will be described below. Note that the same reference numerals in the following description denote constituent elements having almost the same functions and arrangements, and a repetitive description will be made only when required.

Top movement based on which a respiratory gated dynamic scan is performed in a wide range according to the second embodiment and dynamic scan will be described first. For the sake of a concrete description to be given below, assume that respiratory gated dynamic scan includes three dynamic scans. However, this embodiment is not limited to this. For example, the number of times of dynamic scan may be two or four or more.

The operator designates an imaging range in a respiratory gated dynamic scan in a wide range on, for example, a setting window in FIG. 10 via an operation unit 60. If the designated imaging range exceeds an imaging range in one dynamic scan (i.e., the imaging rage is wide), a scan control unit 46 calculates the number of times (set number of times) of dynamic scan and the number of times of top movement to be executed in a respiratory gated dynamic scan in a wide range based on the designated imaging range and an imaging range in each dynamic scan. The scan control unit 46 sets the calculated number of times of dynamic scan and the calculated number of times of top movement as scanning conditions.

FIG. 15 is a graph showing the relationship between the scan position and the time in a respiratory gated dynamic scan in a wide range. As shown in FIG. 15, a top 28 in the second embodiment is stopped during an X-ray irradiation period and moved during stoppage of X-ray irradiation under the control of the scan control unit 46. For example, the apparatus performs X-ray irradiation at the first scan position to perform a dynamic scan on the first scan region. After X-ray irradiation is stopped, the top 28 is moved by a predetermined amount and placed at the second scan position. The apparatus then performs X-ray irradiation at the second scan position to perform a dynamic scan on the second scan region. After X-ray irradiation is stopped, the top 28 is moved by a predetermined amount to be placed at the third scan position. The apparatus performs X-ray irradiation at the third scan position to perform a dynamic scan on the third scan region. When the X-ray irradiation is stopped, the respiratory gated dynamic scan in the wide range is terminated. As described above, in a respiratory gated dynamic scan in a wide range, the top 28 is intermittently moved. Note that the moving amount of the top 28 per operation is set in advance.

The shape of a scan region in a respiratory gated dynamic scan in a wide range will be described next. FIG. 16 is a view showing the shape of a designated scan region (a scan region in a respiratory gated dynamic scan in a wide range) in a case in which each scan region has a shape obtained by combining a circular cone and a column like those shown in FIG. 7. FIG. 17 is a view showing the shape of a designated scan region in a case in which each scan is performed in a columnar shape like that shown in FIG. 8 or 9. As shown in FIG. 16 or 17, the respective scan regions may overlap. In this case, overlap portions may be removed at the time of reconstruction or image combining operation or may be combined by weighted averaging.

Figure 19:
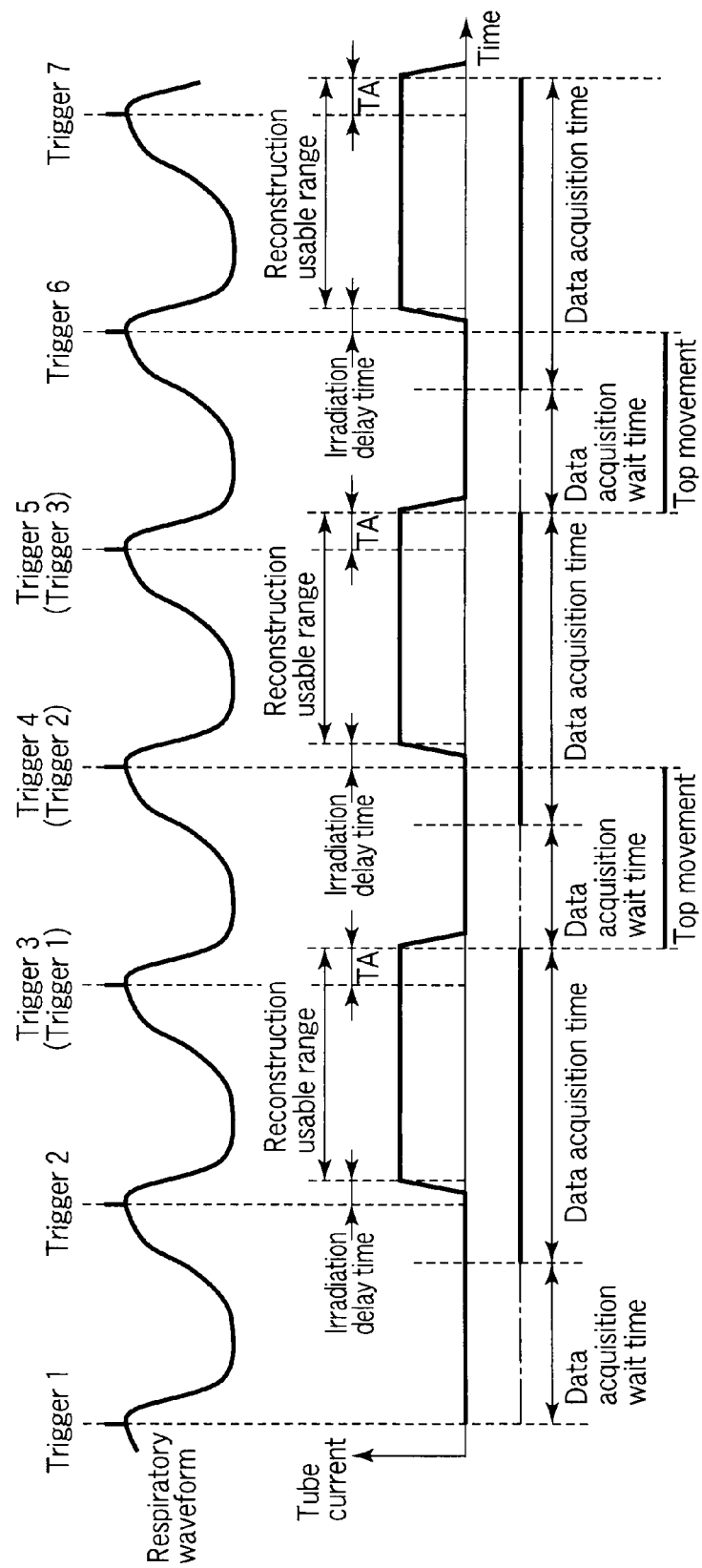
FIG. 19 is a sequence chart associated with the respiratory gated dynamic scan in FIG. 18.

An example of the operation in a respiratory gated dynamic scan according to the second embodiment will be described next with reference to FIGS. 18 and 19. FIG. 18 is a flowchart showing a typical procedure for control processing for a respiratory gated dynamic scan performed by a system control unit 64 according to the second embodiment. FIG. 19 is a sequence chart associated with the respiratory gated dynamic scan according to the second embodiment. Note that the same reference numerals as in the first embodiment denote the same operations in the second embodiment, and a description of them will be omitted. In addition, the calculation of average respiratory cycle and the setting of scanning conditions in the second embodiment are performed in the same manner as in the first embodiment, and hence a description of them will be omitted.

When the operator presses the "execute scan" button, the system control unit 64 starts a respiratory gated dynamic scan in a wide range. First of all, the system control unit 64 waits for the input of a trigger signal (first trigger signal) from the measuring device 100 (step S1). The system control unit 64 waits for the lapse of a data acquisition wait time from the input of the first trigger signal (step S2). When the data acquisition wait time has elapsed from the input of the first trigger signal (YES in step S2), the system control unit 64 causes the scan control unit 46 to start data acquisition (step S3). When the acquisition of projection data starts, the system control unit 64 waits for the input of the next trigger signal (second trigger signal) from the measuring device 100 (step S4). When the second trigger signal is input (YES in step S4), the system control unit 64 controls the scan control unit 46 to start X-ray irradiation (step S5). When X-ray irradiation starts, the system control unit 64 waits for the input of the next trigger signal (third trigger signal) from the measuring device 100 (step S6). When the third trigger signal is input (YES in step S6), the system control unit 64 waits for the lapse of the reconstruction compensation time TA from the input of the third trigger signal (step S7). When the reconstruction compensation time TA has elapsed from the input of the third trigger signal (YES in step S7), the system control unit 64 controls the scan control unit 46 to stop X-ray irradiation and the acquisition of projection data (step S8).

When X-ray irradiation and the acquisition of projection data stop, the system control unit 64 determines whether to terminate a respiratory gated dynamic scan in a wide range (step S9). For example, the system control unit 64 compares the set number of times of dynamic scan with the execution number of times to determine whether to terminate the respiratory gated scan.

Upon determining that the execution number of times of dynamic scan is smaller than the set number of times, the system control unit 64 determines to continue the respiratory gated dynamic scan (NO in step S9). Upon determining to continue the respiratory gated dynamic scan, the system control unit 64 causes the scan control unit 46 to move the top 28 (step S10). In step S10, the scan control unit 46 controls the top driving unit 32 to make the top support mechanism 30 move the top 28 by a predetermined amount to place the top 28 at the scan position of the next dynamic scan. When the top 28 is moved, the system control unit 64 advances to step S2. In step S2, the system control unit 64 waits for the lapse of the data acquisition wait time from the input of the third trigger signal. The system control unit 64 repeats the processing from step S2 to step S9 in the same manner until the execution number of times coincides with the set number of times in step S9. With this operation, a dynamic scan is performed on a plurality of scan regions.

Note that when, for example, the respiratory motion of the subject abruptly quickens, the next trigger signal may be generated during the movement of the top 28 or X-ray irradiation may start during the movement of the top 28. In order to prevent such a situation, when a trigger signal is input during the movement of the top 28, the system control unit 64 can delay the start of X-ray irradiation until the input of the next trigger signal by controlling the scan control unit 46.

Upon determining in step S9 that the execution number of times coincides with the set number of times, the system control unit 64 determines to terminate the respiratory gated dynamic scan in the wide range (YES in step S9). The system control unit 64 then terminates the control processing for the respiratory gated dynamic scan according to the second embodiment.

When the control processing for the respiratory gated dynamic scan according to the second embodiment is terminated, a reconstruction unit 52 reconstructs the data of a plurality of three-dimensional images associated with a plurality of scan regions. In this case, the reconstruction unit 52 reconstructs the data of a three-dimensional image at the respiratory phase designated by the operator for each of a plurality of scan regions included in a scan region in a wide range. For example, the reconstruction unit 52 reconstructs the data of a three-dimensional image at a respiratory phase of 0% for each of a plurality of scan regions.

An image combining unit 54 then performs image combining processing for the data of the three-dimensional images associated with the scan regions to generate the data of a single composite three-dimensional image associated with the scan region in the wide range. In the second embodiment, since the respiratory phases in the respective scan regions accurately match each other, it is possible to generate the data of a composite three-dimensional image with little positional shifts and the like between the three-dimensional images. When the data of the composite three-dimensional image is generated, a three-dimensional image processing unit 56 performs three-dimensional image processing for the data of the composite three-dimensional image to generate the data of a display image (to be referred to as a composite display image hereinafter) associated with the scan region in the wide range. A display unit 58 then displays the generated composite display image. For example, the display unit 58 displays a plurality of composite display images associated with a plurality of respiratory phases in chronological order in a moving image format as in the first embodiment.

With the above arrangement, the X-ray CT apparatus according to the second embodiment controls the start timing of top movement as well as the start timing of X-ray irradiation or projection data acquisition in accordance with the generation timing of a trigger signal (the input timing for the X-ray CT apparatus). Therefore, the X-ray CT apparatus according to the second embodiment can automatically repeat top movement and a dynamic scan in synchronism with the respiratory motion of the subject. This makes it unnecessary for the operator to determine the movement start timing of the top 28 or the X-ray irradiation start timing. This makes it possible to secure a scan time without excess or deficiency in accordance with the respiratory motion of the subject. Therefore, the X-ray CT apparatus according to the second embodiment can execute a dynamic scan on the subject over nearly one respiratory cycle upon minimizing the exposure dose of the subject. In addition, the X-ray CT apparatus according to the second embodiment can reduce the load on the operator which is associated with a respiratory gated dynamic scan over a wide range.

(First Modification)

The display unit 58 may display a sequence chart indicating the timing of at least one of a trigger, respiratory waveform, X-ray irradiation, data acquisition, and bed movement like those shown in FIG. 13 or 19 in chronological order. Illustrating a sequence chart allows the operator or the like to precisely examine the timing of each operation in association with respiratory phases.

(Second Modification)

In order to reduce the exposure dose for obtaining the same image quality (image SD), the scan control unit 46 may control the X-ray tube 16 to decrease the intensity of X-rays when it is located on the front or rear side of a subject and to increase the intensity of X-rays when it is located on a side of the subject. It is possible to change the dose of X-rays in this manner by changing a tube current, for example, in the form of a sine curve in accordance with the rotational angle of the X-ray tube 16. Scanograms may be used to obtain proper tube currents.

(Third Modification)

In step S5 described above, the scan control unit 46 starts X-ray irradiation at the time of the input of the second trigger signal. However, this embodiment is not limited to this. For example, the scan control unit 46 may start X-ray irradiation after the lapse of a predetermined time from the input of the second trigger. The operator can arbitrarily set this predetermined time via the operation unit 60. The predetermined time is not specifically limited, but may be set to, for example, 5% of a respiratory cycle, i.e., about 0.5 sec. Providing the predetermined time can accurately decide the end time of a respiratory gated dynamic scan. This makes it possible to bring the time of a respiratory gated dynamic scan close to nearly one respiratory cycle and reduce the exposure dose of the subject P as compared with the prior art in which the detection timing of the next trigger signal is predicted from the detection timing of a given trigger signal, and an instruction to start X-ray irradiation is issued at the predicted timing. The X-ray CT apparatus according to the third modification can therefore generate X-rays immediately after the lapse of a predetermined time from the input of a trigger signal and keep generating X-rays only within nearly one respiratory cycle starting from the time point.

(Fourth Modification)

In this embodiment, the measuring device 100 is a respiration sensor which measures the respiratory motion of the subject P. However, the measuring device 100 according to the embodiment may be a device which measures the periodic motion of an organ of the subject. The measuring device 100 of this type includes an electrocardiograph which electrically measures the periodic pulsation of the heart. In this case, the input unit 42 repeatedly inputs trigger signals originating from a specific cardiac phase from the measuring device 100. In step S5, the scan control unit 46 starts X-ray irradiation immediately after the input of the second trigger. In addition, the scan control unit 46 may start X-ray irradiation after the lapse of a predetermined time from the input of the second trigger. The operator can arbitrarily set this predetermined time via the operation unit 60. The predetermined time is not specifically limited, but may be set to, for example, 5% of a heartbeat period, i.e., about 0.2 sec. This allows the X-ray CT apparatus according to the fourth modification to execute a dynamic scan on a subject over nearly one heartbeat period upon minimizing the exposure dose of the subject.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
an X-ray tube configured to generate X-rays;
an X-ray detector configured to detect X-rays generated from the X-ray tube and transmitted through a subject and generate an electrical signal corresponding to the detected X-rays;
an acquisition unit configured to acquire the projection data corresponding to the electrical signal via the X-ray detector;
a rotating mechanism configured to rotatably support the X-ray tube and the X-ray detector around the subject;
an input unit configured to repeatedly input trigger signals originating from a specific phase of a periodic motion of a body of the subject or a periodic motion of an organ of the subject, the trigger signals being supplied from a measuring device which measures the periodic motion;
a control unit configured to cause the X-ray tube to start generating X-rays on the basis of an input of a first trigger signal of the repeatedly input trigger signals, and to cause the X-ray tube to stop generating X-rays on the basis of an input of a second trigger signal next to the first trigger signal in order to repeatedly scan the subject over substantially one period of the movement while a scan position is fixed; and
a reconstruction unit configured to reconstruct data of an image associated with the subject based on the projection data.

2. The apparatus according to claim 1, wherein the measuring device measures respiratory motion of the subject.

3. The apparatus according to claim 2, wherein the control unit starts generation of the X-rays immediately after the first trigger signal is input to the input unit.

4. The apparatus according to claim 2, wherein the control unit causes the X-ray tube to start generating X-rays after the lapse of a predetermined time from an input of the first trigger signal to the input unit.

5. The apparatus according to claim 2, wherein the control unit causes the X-ray tube to start generating X-rays after the lapse of an irradiation delay time from an input of the first trigger signal to the input unit.

6. The apparatus according to claim 2, wherein the control unit causes the X-ray tube to start generating X-rays after the lapse of a total time of an irradiation delay time and a first predetermined time from an input of the first trigger signal to the input unit.

7. The apparatus according to claim 2, wherein the control unit causes the X-ray tube to stop generating X-rays after the lapse of a second predetermined time from an input of the second trigger signal to the input unit.

8. The apparatus according to claim 7, wherein the second predetermined time is a time required for the X-ray tube to rotate through 360° when the reconstruction unit uses a full reconstruction method, and is a time required for the X-ray tube to rotate through 180°+fan angle when the reconstruction unit uses a half reconstruction method.

9. The apparatus according to claim 7, wherein the second predetermined time is a sum of a time required for the X-ray tube to rotate through 360° and an irradiation delay time when the reconstruction unit uses a full reconstruction method, and is a sum of a time required for the X-ray tube to rotate through 180°+fan angle and the irradiation delay time when the reconstruction unit uses a half reconstruction method.

10. The apparatus according to claim 7, wherein the second predetermined time is a sum of a time required for the X-ray tube to rotate through 360°, an irradiation delay time, and a third predetermined time when the reconstruction unit uses a full reconstruction method, and is a sum of a time required for the X-ray tube to rotate through 180°+fan angle, the irradiation delay time, and the third predetermined time when the reconstruction unit uses a half reconstruction method.

11. The apparatus according to claim 2, wherein the control unit causes the X-ray tube to start generating X-rays when the first trigger signal is input to the input unit, and causes the X-ray tube to stop generating X-rays after the lapse of a second predetermined time from an input of the second trigger signal by the input unit.

12. The apparatus according to claim 2, wherein the control unit causes the X-ray tube to start generating X-rays after the lapse of a first predetermined time from an input of the first trigger signal by the input unit, and causes the X-ray tube to stop generating X-rays after the lapse of a second predetermined time from an input of the second trigger signal by the input unit.

13. The apparatus according to claim 1, wherein the control unit causes the X-ray tube to stop generating X-rays after the lapse of a second predetermined time from an input of the second trigger signal by the input unit, the second predetermined time being a time required for the X-ray tube to rotate through 360° when the reconstruction unit uses a full reconstruction method, and being a time required for the X-ray tube to rotate through 180°+fan angle when the reconstruction unit uses a half reconstruction method.

14. The apparatus according to claim 1, wherein the control unit causes the X-ray tube to stop generating X-rays after the lapse of a second predetermined time from an input of the second trigger signal by the input unit, the second predetermined time being a sum of a time required for the X-ray tube to rotate through 360° and an irradiation delay time when the reconstruction unit uses a full reconstruction method, and being a sum of a time required for the X-ray tube to rotate through 180°+fan angle and the irradiation delay time when the reconstruction unit uses a half reconstruction method.

15. The apparatus according to claim 1, wherein the control unit causes the X-ray tube to stop generating X-rays after the lapse of a second predetermined time from an input of the second trigger signal by the input unit, the second predetermined time being a sum of a time required for the X-ray tube to rotate through 360°, an irradiation delay time, and a third predetermined time when the reconstruction unit uses a full reconstruction method, and being a sum of a time required for the X-ray tube to rotate through 180°+fan angle, the irradiation delay time, and the third predetermined time when the reconstruction unit uses a half reconstruction method.

16. The apparatus according to claim 1, wherein the control unit causes the X-ray tube to start generating X-rays when the first trigger signal is input to the input unit, and causes the X-ray tube to stop generating X-rays after the lapse of a second predetermined time from an input of the second trigger signal to the input unit.

17. The apparatus according to claim 1, wherein the control unit causes the X-ray tube to start generating X-rays after the lapse of a first predetermined time from an input of the first trigger signal to the input unit, and causes the X-ray tube to stop generating X-rays after the lapse of a second predetermined time from an input of the second trigger signal to the input unit.

18. The apparatus according to claim 1, wherein the reconstruction unit reconstructs data of an image associated with a specific phase based on the projection data, the specific phase being of the respiratory cycle and indicated by an instruction from an operator.

19. The apparatus according to claim 1, further comprising a display unit configured to display a display image in accordance with the data of the image.

20. The apparatus according to claim 1, which further comprises
a top on which the subject is placed, and
a moving mechanism configured to movably support the top along a rotation axis of the rotating mechanism, and in which
the control unit controls generation of X-rays from the X-ray tube, acquisition of projection data by the acquisition unit, and intermittent movement of the top by the moving mechanism in synchronism with the input trigger signal in order to repeatedly scan each of a plurality of scan regions associated with the subject over substantially one period of the motion.

21. The apparatus according to claim 20, wherein the reconstruction unit reconstructs data of a plurality of images associated with the scan regions based on the projection data.

22. The apparatus according to claim 20, wherein the control unit causes the X-ray tube to start generating X-rays on the basis of an input of the first trigger signal to the input unit, and causes the X-ray tube to stop generating X-rays and moves the top by a predetermined amount on the basis of an input of the second trigger signal to the input unit.

23. The apparatus according to claim 22, wherein the control unit causes the X-ray tube to stop generating X-rays after the lapse of a predetermined time from the input of the second trigger signal to the input unit and moves the top by a predetermined amount.

24. The apparatus according to claim 20, wherein the reconstruction unit reconstructs data of the images associated with a specific phase based on the projection data, the specific phase being indicated by an instruction from an operator.

25. The apparatus according to claim 24, further comprising an image combining unit configured to generate data of a single image associated with the specific phase associated with the scan regions, based on the data of the images.

26. An X-ray computed tomography apparatus comprising:
an X-ray tube configured to generate X-rays;
an X-ray detector configured to detect X-rays generated from the X-ray tube and transmitted through a subject and generate an electrical signal corresponding to the detected X-rays;
an acquisition unit configured to acquire the projection data corresponding to the electrical signal via the X-ray detector;
a rotating mechanism configured to rotatably support the X-ray tube and the X-ray detector around the subject;
an input unit configured to repeatedly input trigger signals originating from a specific respiratory phase of a respiratory cycle of a respiratory motion of the subject from a measuring device which measures the respiratory motion;
a control unit configured to control generation of X-rays from the X-ray tube and acquisition of projection data by the acquisition unit in synchronism with the input trigger signals in order to repeatedly scan the subject over substantially one respiratory cycle while a scan position is fixed; and
a reconstruction unit configured to reconstruct data of an image associated with the subject based on the projection data.

* * * * *